(12) United States Patent
Sumiya

(10) Patent No.: US 6,761,455 B2
(45) Date of Patent: Jul. 13, 2004

(54) OPHTHALMIC APPARATUS

(75) Inventor: Toshifumi Sumiya, Nukata-gun (JP)

(73) Assignee: Nidek Co., Ltd., Gamagori (JP)

(*) Notice: Subject to any disclaimer, the term of this patent is extended or adjusted under 35 U.S.C. 154(b) by 0 days.

(21) Appl. No.: 10/054,851

(22) Filed: Jan. 25, 2002

(65) Prior Publication Data
US 2002/0101567 A1 Aug. 1, 2002

(30) Foreign Application Priority Data
Jan. 31, 2001 (JP) ......................................... 2001-024029

(51) Int. Cl.[7] .............................................. A61B 3/10
(52) U.S. Cl. ..................................................... 351/221
(58) Field of Search ................................. 351/205, 206, 351/214, 221; 348/262, 263, 264; 356/456; 600/476, 443, 452, 318, 310, 407, 477; 606/4

(56) References Cited

U.S. PATENT DOCUMENTS 5,539,517 A * 7/1996 Cabib et al. ................ 356/456
6,276,798 B1 * 8/2001 Gil et al. .................... 351/206

FOREIGN PATENT DOCUMENTS

JP         A 8-266471         10/1996

OTHER PUBLICATIONS

"ImSpector" product brochure; Kawasaki Steel Techno–Research Co. (1999).
"ImSpectorimaging spectrograph" product brochure; Spectral Imaging Ltd., Kaitovayla, Finland (undated).

* cited by examiner

Primary Examiner—George Manuel
(74) Attorney, Agent, or Firm—Oliff & Berridge, PLC

(57) ABSTRACT

The present invention intends to provide an ophthalmic apparatus which enables an examiner to diagnose a patient with cataract and the like in the early stage, and which can be used even for a screening examination and the like. The ophthalmic apparatus comprises an illumination optical system for having illumination light enter an inside of an eye to be examined so that the light scattered and reflected on a fundus of the eye illuminates an anterior part of the eye and a photographing optical system having an imaging spectroscope for obtaining an image including spectral information, for photographing a retroillumination image of the illuminated anterior part of the eye with the imaging spectroscope.

3 Claims, 3 Drawing Sheets

OPHTHALMIC APPARATUS

BACKGROUND OF THE INVENTION

1. Field of the Invention

The present invention relates to an ophthalmic apparatus for photographing a retroillumination image of an eye to be examined.

2. Description of Related Art

Conventionally, a diagnosis of cataract and the like has been carried out mainly by a method based on slit observation with a slit-lamp microscope and observation of a retroillumination image. As a method for diagnosis of the above diseases, such has also been known that an examiner uses an apparatus for sectioning an eye to be examined with slit light and obtaining (photographing) a cross-sectional image of an anterior part of the eye with a photographing optical system disposed based on the Scheimpflug's principle. Then, a diagnosis of a condition of opacity in a crystalline lens and the like is made based on the obtained image.

Under the above-mentioned method, it is possible to diagnose a condition of opacity in a crystalline lens and the like in which cataract has relatively developed, but it is difficult to make a diagnosis in the early stage of cataract. Further, when a slit-lamp microscope and an apparatus for photographing based on the Scheimpflug's principle are used, technical observation by an ophthalmologist is required, and the apparatus is not suitable for a screening examination and the like. Therefore, there has been a problem that a patient cannot be diagnosed with cataract unless he or she notices a sign of the disease and is in its advanced stage.

SUMMARY OF THE INVENTION

The present invention has been made in view of the above circumstances and has an object to overcome the above problems and to provide an ophthalmic apparatus which enables an examiner to diagnose a patient with cataract and the like in the early stage, and which can be used even for a screening examination and the like.

To achieve the objects and in accordance with the purpose of the present invention, as embodied and broadly described herein, an ophthalmic apparatus comprises an illumination optical system for having illumination light enter an inside of an eye to be examined so that the light scattered and reflected on a fundus of the eye illuminates an anterior part of the eye and a photographing optical system having an imaging spectroscope for obtaining an image including spectral information, for photographing a retroillumination image of the illuminated anterior part of the eye with the imaging spectroscope.

In another aspect of the present invention, an ophthalmic apparatus comprises a photographing optical system having a photographing lens, for photographing a retroillumination image of an anterior part of an eye illuminated in light reflected from a fundus of the eye, wherein the photographing optical system has an imaging spectroscope, disposed on an opposite side of the eye with respect to the photographing lens, for obtaining an image including spectral information.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
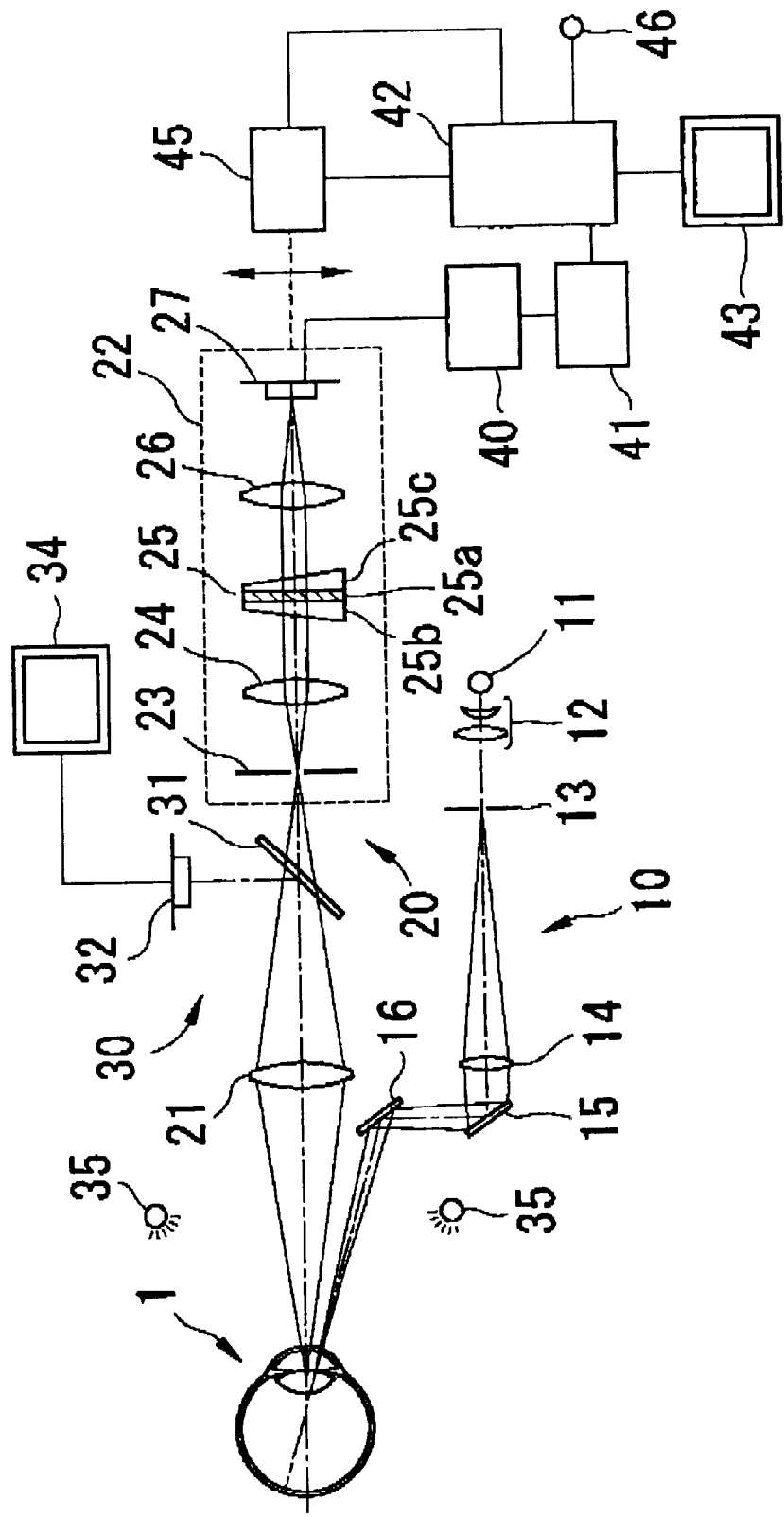
FIG. 1 is a view showing a schematic configuration of an ophthalmic apparatus consistent with the present invention.

A detailed description of one preferred embodiment of an ophthalmic apparatus embodying the present invention will now be given referring to the accompanying drawings. FIG. 1 is a view showing a schematic configuration of an ophthalmic apparatus consistent with the present invention, including an eye 1 to be examined, an illumination optical system 10, a photographing optical system 20, and an observation optical system 30.

The illumination optical system 10 is provided to guide illumination light to the inside of the eye 1, and a slit illumination optical system provided in a regular slit-lamp microscope and the like may be used for the system 10. The illumination light from a halogen lamp 11 converges through a condenser lens 12 on a slit 13. The illumination light having passed through the slit 13 goes through a projecting lens 14 and mirrors 15 and 16 to be guided into (enter) the inside of the eye 1 via its pupil. At this point, an incident optical axis of the illumination light has an angle to incline with respect to an optical axis of the photographing optical system 20 placed on an optical axis of the eye 1. A position of the mirror 16 and its inclination angle are defined so that the illumination light is guided into (enters) the inside of the eye 1 via a periphery of the cornea. In this manner, light reflected on the corneal surface is prevented from entering the photographing optical system 20 and from being noise to the retroillumination image. Although FIG. 1 illustrates an image of the slit 13 formed on the pupil, forming the image thereon is not always required. However, it helps the illumination light bundle become narrow on the pupil so that the light bundle easily passes through the periphery of the pupil.

The illumination light guided into (entered) the inside of the eye 1 reaches the fundus, and it is scattered and reflected thereon to illuminate the optic media (a crystalline lens and the like) of an anterior part of the eye 1 from the rear.

The photographing optical system 20 photographs a retroillumination image of the anterior part of the eye 1 illuminated from the rear in the illumination light scattered and reflected on the fundus. A photographing lens 21 forms an image of a crystalline lens on an imaging spectroscope 22 disposed behind. The imaging spectroscope 22 includes a slit 23 having an infinitesimal lineal aperture, a lens 24, a Prism-Grating-Prism 25(referred to as the PGP hereinafter), a lens 26, and a CCD camera 27 having a sensitivity to the visible region. The slit 23 is placed at a position conjugate with a region targeted for photographing with respect to the photographing lens 21. The PGP 25 is a spectral optical member constituted of prisms 25b and 25c sandwiching a transmissive grating 25a therebetween. It should be noted that the camera 27 may be for photographing monochrome images. The image formed on the imaging spectroscope 22 is dispersed there so that a retroillumination image including spectral information is formed.

Figure 2:
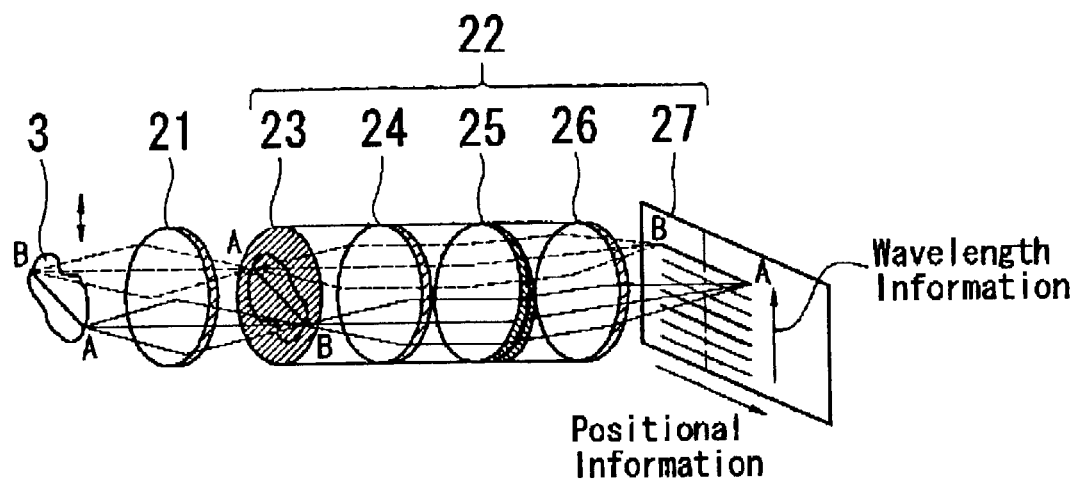
FIG. 2 is a view showing a mechanism of an imaging spectroscope.

FIG. 2 is a view showing the mechanism of the imaging spectroscope 22. The lens 21 forms an image of an object 3 targeted for photographing (a region targeted for photographing) on the slit 23. While the image of the entire object 3 is formed on the slit 23, only the light bundle illuminating the aperture of the slit 23 goes into the lens 24 disposed behind to become a parallel light bundle. Then, the parallel light bundle enters the PGP 25 to be dispersed according to wavelength. After that, an image is formed again by the lens 26 on the camera 27 (on its photographic element). The image on the camera 27 is constituted of the lineal area images of the slit 23 lined up according to wavelength since the light bundle is dispersed according to wavelength by the PGP 25. That is, the longitudinal direction of the slit 23 provides information about each position of the lineal area, and the direction perpendicular to the longitudinal direction provides information about each wavelength. The positional information and spectral information about the entire area of the object 3 can be obtained by capturing the above-mentioned information about the position and wavelength as one image and by scanning the lineal area across the entire object 3.

The observation optical system 30 shares the photographing lens 21 with the photographing optical system 20. The system 30 includes a half mirror 31 (or a dichroic mirror reflecting infrared light and transmitting visible light) and a CCD camera 32 disposed on the reflecting side of the half mirror 31. The image of the anterior part of the eye 1 illuminated with an infrared illumination light source 35 is formed on the camera 32 via the photographing lens 21 and the half mirror 31, and it is shown on a monitor 34 for observation.

An image signal outputted from the camera 27 is given to an image memory unit 40 so that a photographed image is stored therein. The image stored in the image memory unit 40 is outputted to a spectrum analyzing unit 41 where the spectral information is analyzed. A control unit 42 controls the entire apparatus, and it is connected with the spectrum analyzing unit 41, a monitor 43 showing an analytical result, a scanning drive unit 45 for scanning by sequentially moving the imaging spectroscope 22 in the direction of the slit width of the slit 23, a photographing switch 46, and the like.

A description will be given about operations of the apparatus having the configuration described above. The examiner performs alignment of the eye 1 with the apparatus under a known operational method while he or she observes the image of the anterior part of the eye 1 on the monitor 34. Upon completion of the alignment, the illumination light from the illumination optical system 10 is guided to (enters) the inside of the eye 1 via the periphery of its pupil. The illumination light having entered the inside of the eye 1 is scattered and reflected on the fundus and returns to the front of the eye 1. Part of the light passes thorough the crystalline lens and the cornea and comes out of the eye 1 again. The light converges on the slit 23 of the imaging spectroscope 22 by the photographing lens 21 so that the image of the inside of the crystalline lens is formed on the slit 23. That is, the object 3 in FIG. 2 corresponds to the region of the crystalline lens targeted for photographing. The light of the image formed on the slit 23 passes only through the aperture of the slit 23, and it is made to be the parallel light bundle by the lens 24. Then, it is dispersed according to wavelength by the PGP 25, and an image is formed by the lens 26 on the camera 27.

Figure 3:
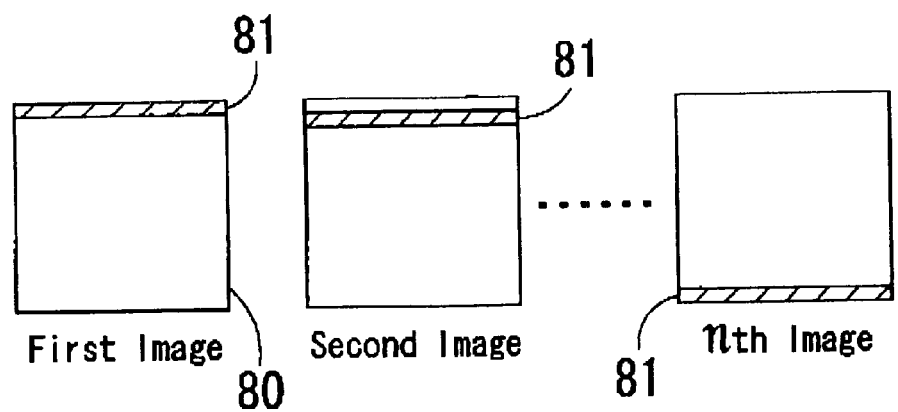
FIG. 3 is a view illustrating a procedure of scanning a lineal photographing area across an entire photographing area.

By pressing the photographing switch 46, the camera 27 photographs one image including the positional and spectral information about the lineal area corresponding to the aperture of the slit 23. The control unit 42 controls the drive of the scanning drive unit 45 in accordance with a signal from the photographing switch 46. As shown in FIG. 3, photographing a lineal photographing area 81 begins at one end of an entire photographing area 80 of the crystalline lens which is the region targeted for photographing. Photographing the subsequent images is performed by moving the imaging spectroscope 22 in the direction of the slit aperture width of the slit 23 (the direction perpendicular to the longitudinal direction of the slit aperture) by its width (by scanning the entire photographing area 80). Then, the camera 27 sequentially photographs n images of the lineal area 81 until the scanning reaches the other end of the entire area 80. The information contained in the images, which are photographed every time the imaging spectroscope 22 moves, is stored in the image memory unit 40 in sequence.

The spectrum analyzing unit 41 analyzes the spectra of the n images stored in the image memory unit 40. The analytical result is outputted on the monitor 43 via the control unit 42. In a case where an unusual change in transmission and the like at a certain wavelength is found in the crystalline lens, the examiner may be able to make a diagnosis in the early stage of cataract by analyzing the change in the spectra of the images. It should be noted that the sensitivity of the camera 27 with respect to wavelengths should be calibrated in advance for analyzing a change in a spectrum.

As for analyzing the images, for example, light intensity of each wavelength (or a wavelength band) in one image is obtained at each point of the lineal photographing area. This procedure is performed for the first image through the $n^{th}$ image obtained by scanning so that light intensity of each wavelength may be obtained at each point in the entire photographing area (i.e. the area of the inside of the pupil targeted for photographing).

Figure 4:
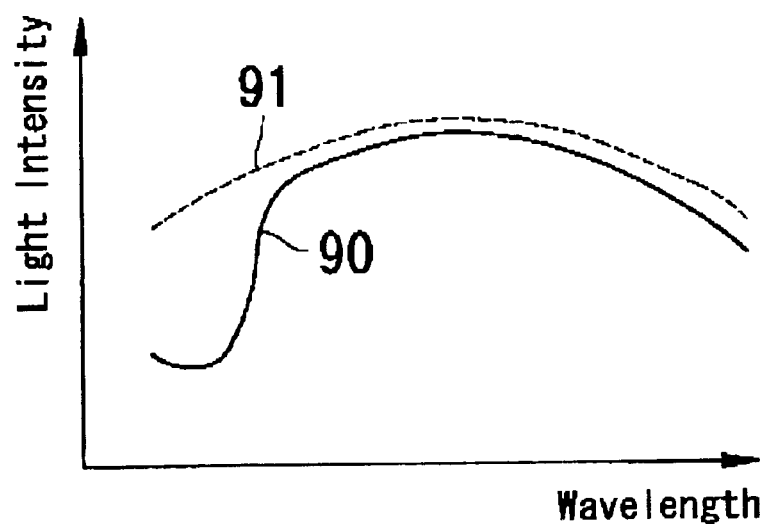
FIG. 4 is a view showing an example of an analytical result of an image.

In FIG. 4, a graph 90 of a wavelength characteristic shown in a solid line depicts light intensity with respect to wavelengths at a certain point, which is obtained in the above-described manner. When a graph 91 shown in a dotted line represents an average wavelength characteristic at another point or a targeted area, the point with the wavelength characteristic represented by the solid line 90 indicates that transmission of the short wavelengths is especially deteriorated.

Figure 5:
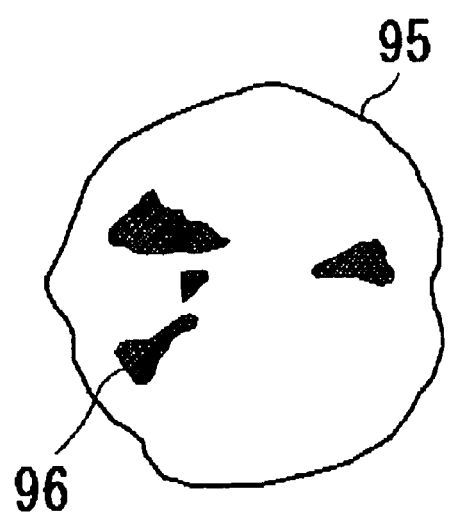
FIG. 5 is a view showing another example of an analytical result of an image.

Further, in FIG. 5, the information about the light intensity at a certain wavelength band (for example, 400 nm to 410 nm) is obtained at each point, and a distribution is obtained by binarizing the information at an appropriate threshold level. In the figure, a diagonally shaded part 96 in a pupil region 95 shows a binarized part where the light intensity is low. In other words, the diagonally shaded part 96 is obtained as the part having a low transmission characteristic with respect to a specific wavelength band. This analysis is carried out for other wavelength bands to obtain an unusual change in transmission of every wavelength.

Also, since the light intensity of each wavelength in the lineal area is included in one photographed image, a color image of the lineal area may be obtained by superposing one lineal image including the light intensity of each wavelength on another. When all the images obtained by scanning are arranged from the first to n$^{th}$ images, a color image of the entire area can be obtained. This color image is constituted of the lineal images, and each lineal image (each point) includes spectral information. Thus, the color image also includes spectral information in itself. An unusual change in wavelengths may be assessed by displaying the color image on the monitor 43.

In addition, since a spectral retroillumination image of an eye with an opaque crystalline lens due to cataract provides its spectral transmission characteristic, an analytical result can also be used for simulating how a patient with cataract views things in color. For example, with reference to a color image of an object or scenery viewed by a person with a normal crystalline lens, an image, of which colors are changed based on the analytical result of the spectral transmission characteristic of the patient with cataract, can be displayed on the monitor 43.

In the preferred embodiment presented above, a description is given only about an apparatus designed specifically for photographing a retroillumination image. However, the present invention can be applied to an apparatus in which a unit including the photographing optical system 20 is attached to an existing slit-lamp microscope to partially use an illumination optical system and an observation optical system included in the slit-lamp microscope.

As described above, according to the present invention, it is possible to make a diagnosis of cataract and the like in the early stage and to easily carry out a screening examination and the like. Also, detection of an unusual change in a transmission characteristic at a wavelength allows an examiner to make a detailed diagnosis of cataract and the like.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus comprising:
   an illumination optical system for having illumination light enter an inside of an eye to be examined through a pupil of the eye so that the light scattered and reflected on a fundus of the eye illuminates a crystalline lens of the eye from behind;
   a photographing optical system having an imaging spectroscope, for photographing illuminated crystalline lens one-dimensionally, the imaging spectroscope including a slit having a lineal aperture, a spectral optical member, and a two-dimensional photographing element;
   an analysis unit which analyzes a one-dimensional transmission characteristic of the crystalline lens based on information on an image obtained by the photographing element; and
   a display unit which displays a result of analysis by the analysis unit.

2. The ophthalmic apparatus according to claim 1, further a scanning unit which moves the imaging spectroscope in a direction approximately perpendicular to a longitudinal direction of the aperture.

3. An ophthalmic apparatus comprising:
   an illumination optical system for having illumination light enter an inside of an eye to be examined through a pupil of the eye so that the light scattered and reflected on a fundus of the eye illuminates a crystalline lens of the eye from behind;
   a photographing optical system having an imaging spectroscope, for photographing the illuminated crystalline lens one-dimensionally, the imaging spectroscope including a slit having a lineal aperture, a spectral optical member, and a two-dimensional photographing element;
   a scan and control unit which moves a photographing position of the photographing optical system in a direction approximately perpendicular to a direction of the one-dimension to obtain information on an image at each position of movement;
   an analysis unit which analyzes a two-dimensional transmission characteristic of the crystalline lens based on the information on the image obtained by the photographing element; and
   a display unit which displays a result of analysis by the analysis unit.

\* \* \* \* \*